US012620128B2

(12) United States Patent (10) Patent No.: US 12,620,128 B2
Andersson et al. (45) Date of Patent: May 5, 2026

(54) METHOD TO DETERMINE UNIVERSAL HEAT MAP

(71) Applicant: TOBII AB, Danderyd (SE)

(72) Inventors: Richard Andersson, Danderyd (SE);
Ihor Lomachenko, Danderyd (SE);
Yevhen Dobronohov, Danderyd (SE);
Ihor Bielousov, Danderyd (SE);
Oleksandra Kunatova, Danderyd (SE)

(73) Assignee: Tobii AB, Danderyd (SE)

( * ) Notice: Subject to any disclaimer, the term of this patent is extended or adjusted under 35 U.S.C. 154(b) by 176 days.

(21) Appl. No.: 18/628,899

(22) Filed: Apr. 8, 2024

(65) Prior Publication Data

US 2024/0320854 A1 Sep. 26, 2024

(51) Int. Cl.
*G06T 7/73* (2017.01)
*A61B 5/16* (2006.01)
(Continued)

(52) U.S. Cl.
CPC ................ *G06T 7/73* (2017.01); *A61B 5/163* (2017.08); *A61B 5/168* (2013.01); *G06F 3/013* (2013.01);
(Continued)

(58) Field of Classification Search
CPC .................... G06T 7/73; G06T 11/206; G06T 2207/30196; A61B 5/163; A61B 5/168; G06F 3/013
See application file for complete search history.

(56) References Cited

U.S. PATENT DOCUMENTS 9,619,908 B1 * 4/2017 Zuczek .................. G06V 20/48
10,181,078 B1 * 1/2019 Haass .................... G06V 40/19
(Continued)

FOREIGN PATENT DOCUMENTS

KR 20220136288 A 10/2022
KR 20220157643 A 11/2022
(Continued)

OTHER PUBLICATIONS

Swedish Search Report for Application No. 2350413-7, completed on Oct. 27, 2023.
(Continued)

*Primary Examiner* — Daniel F Hajnik
*Assistant Examiner* — Joshua Jungwook Suo
(74) *Attorney, Agent, or Firm* — Christopher Ignatius Moylan

(57) ABSTRACT

A method for an eye tracking system comprising at least one camera configured to provide a heatmap based on an observation of at least one user and comprising the steps of: defining a region to be analysed; receiving an input in the form of a stimulus whereby the stimulus is positioned within the region; determining a first gaze metric comprising gaze point data and gaze duration data, determined in relation to the region comprising the stimulus and over time; determining a second metric related, comprising data different from the first gaze metric, determined in relation to the region comprising the stimulus and over a duration of time; dividing the region into a plurality of sections; processing data related to gaze metrics by allocating values to the sections, so that a heatmap can be generated based on these allocated values and the sections; and mapping the processed data on a heatmap.

12 Claims, 8 Drawing Sheets

(51) Int. Cl.
G06F 3/01            (2006.01)
G06T 11/26           (2026.01)

(52) U.S. Cl.
CPC .... G06T 11/26 (2026.01); G06T 2207/30196
(2013.01)

(56)              References Cited

U.S. PATENT DOCUMENTS

| | | |
|---|---|---|
| 2006/0189886 A1 | 8/2006 | Jones et al. |
| 2006/0203197 A1 | 9/2006 | Marshall et al. |
| 2014/0184550 A1* | 7/2014 | Hennessey .............. G06F 3/041 |
| | | 345/173 |
| 2015/0301597 A1 | 10/2015 | Rogers et al. |
| 2018/0307690 A1* | 10/2018 | Souche .............. G06Q 30/0241 |
| 2020/0104637 A1 | 4/2020 | Kim et al. |

FOREIGN PATENT DOCUMENTS

| | | |
|---|---|---|
| KR | 20220160303 A | 12/2022 |
| WO | 2023004734 A1 | 2/2023 |

OTHER PUBLICATIONS

Venugopal, Divya & Joseph, Amudha & Chandrasekharan, Jyotsna. (2016). Developing an application using eye tracker. 1518-1522. 10.1109/RTEICT.2016.7808086.

Sharafi, Z., Sharif, B., Guéhéneuc, YG. et al. A practical guide on conducting eye tracking studies in software engineering. Empir Software Eng 25, 3128-3174 (2020). https://doi.org/10.1007/s10664-020-09829-4.

Bojko, Agnieszka. (2009). Informative or Misleading? Heatmaps Deconstructed. Human-Computer Interaction. New Trends, 13th International Conference, HCI International 2009, San Diego, CA, USA, Jul. 19-24, 2009, Proceedings, Part I. 30-39. 10.1007/978-3-642-02574-7_4.

Courtemanche, F., Léger, PM., Dufresne, A. et al. Physiological heatmaps: a tool for visualizing users' emotional reactions. Multimed Tools Appl 77, 11547-11574 (2018). https://doi.org/10.1007/s11042-017-5091-1.

* cited by examiner

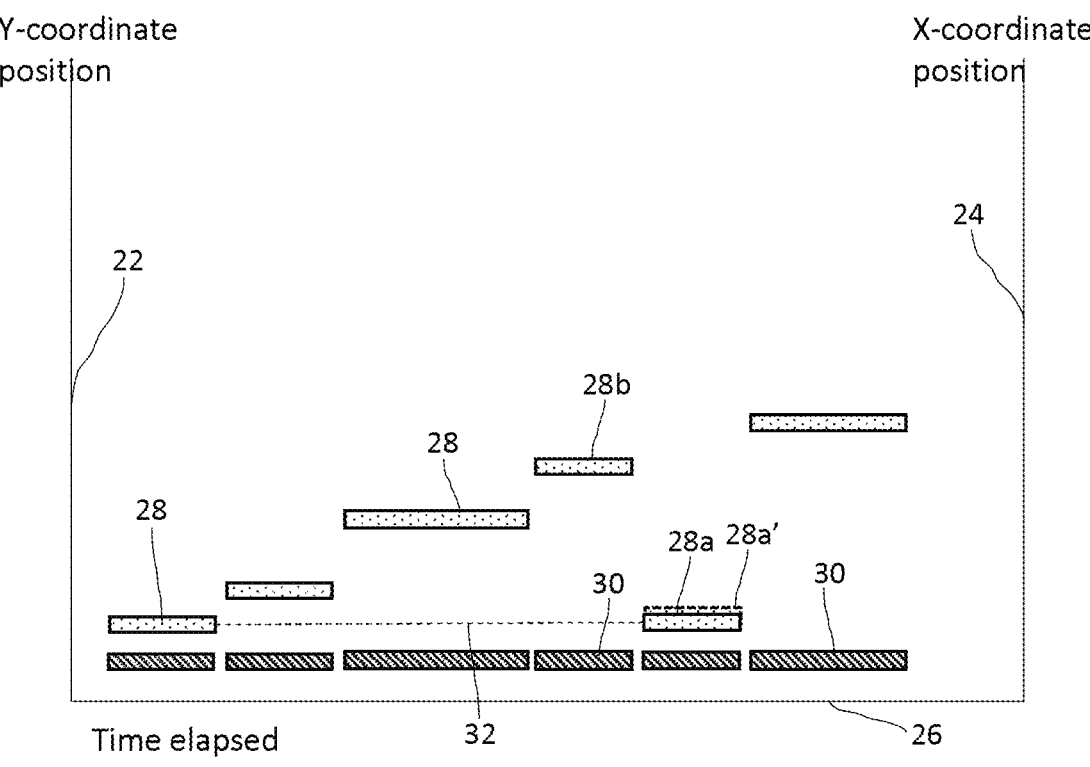

Fig. 5a

This is my text, and it consists of multiple sentences.
Sometimes when a word is difficult to understand, you may
make regression back to previous text to understand it.
Typical examples would be pronouns, like "she" or "them",
and you go back to see who they referred to if you can't
disambiguate it from the text. A sentence may, for example,
be less obvious to decode with multiple potential targets
for a referential expression, like:

14''

"My mom ruined my sister's vacation. She was furious"

In this example it is not obvious who "she" refers to.

Fig. 5b

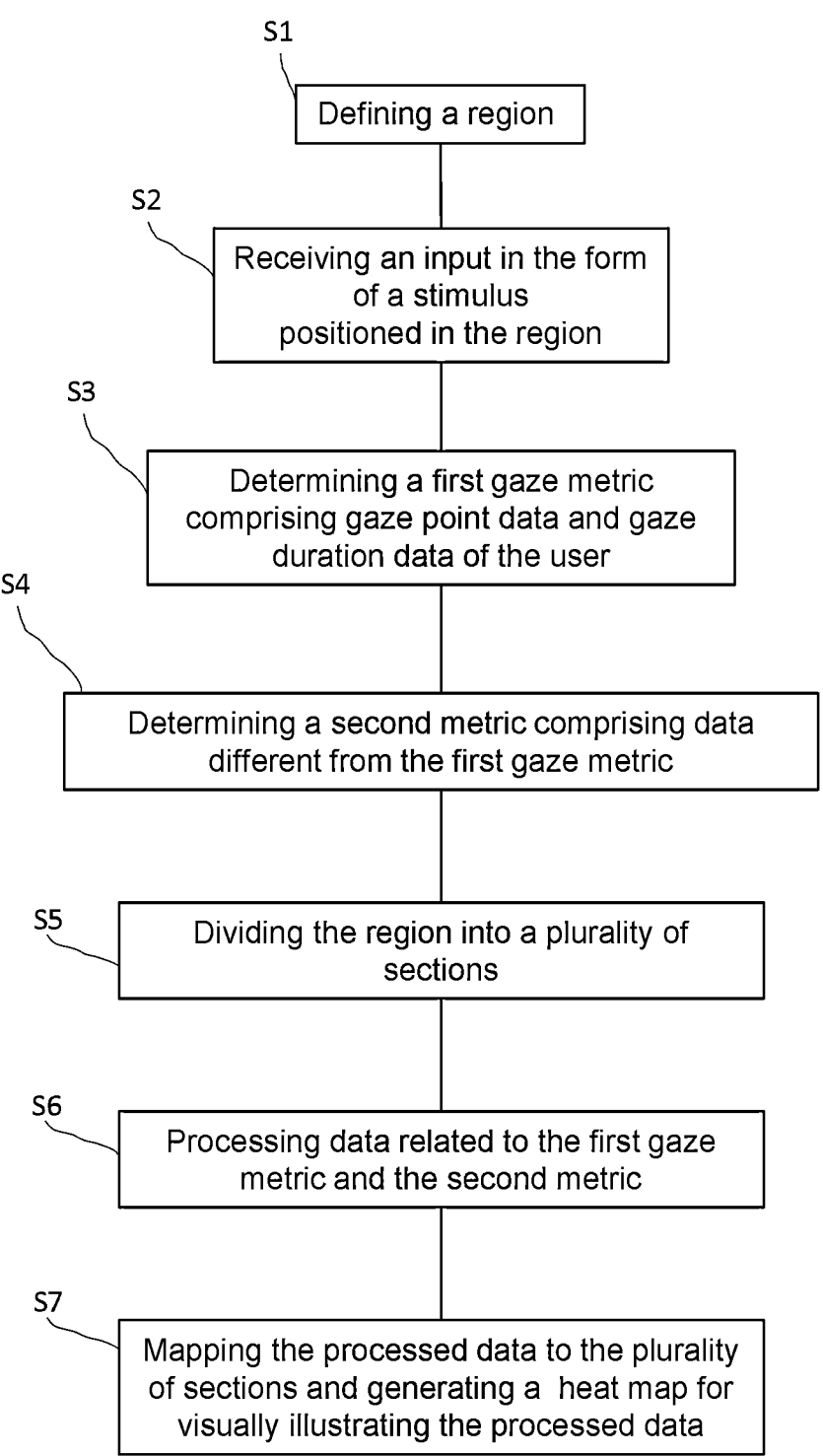

S1

Defining a region

S2

Receiving an input in the form
of a stimulus
positioned in the region

S3

Determining a first gaze metric
comprising gaze point data and gaze
duration data of the user

S4

Determining a second metric comprising data
different from the first gaze metric

S5

Dividing the region into a plurality of
sections

S6

Processing data related to the first gaze
metric and the second metric

S7

Mapping the processed data to the plurality
of sections and generating a  heat map for
visually illustrating the processed data

Fig. 8

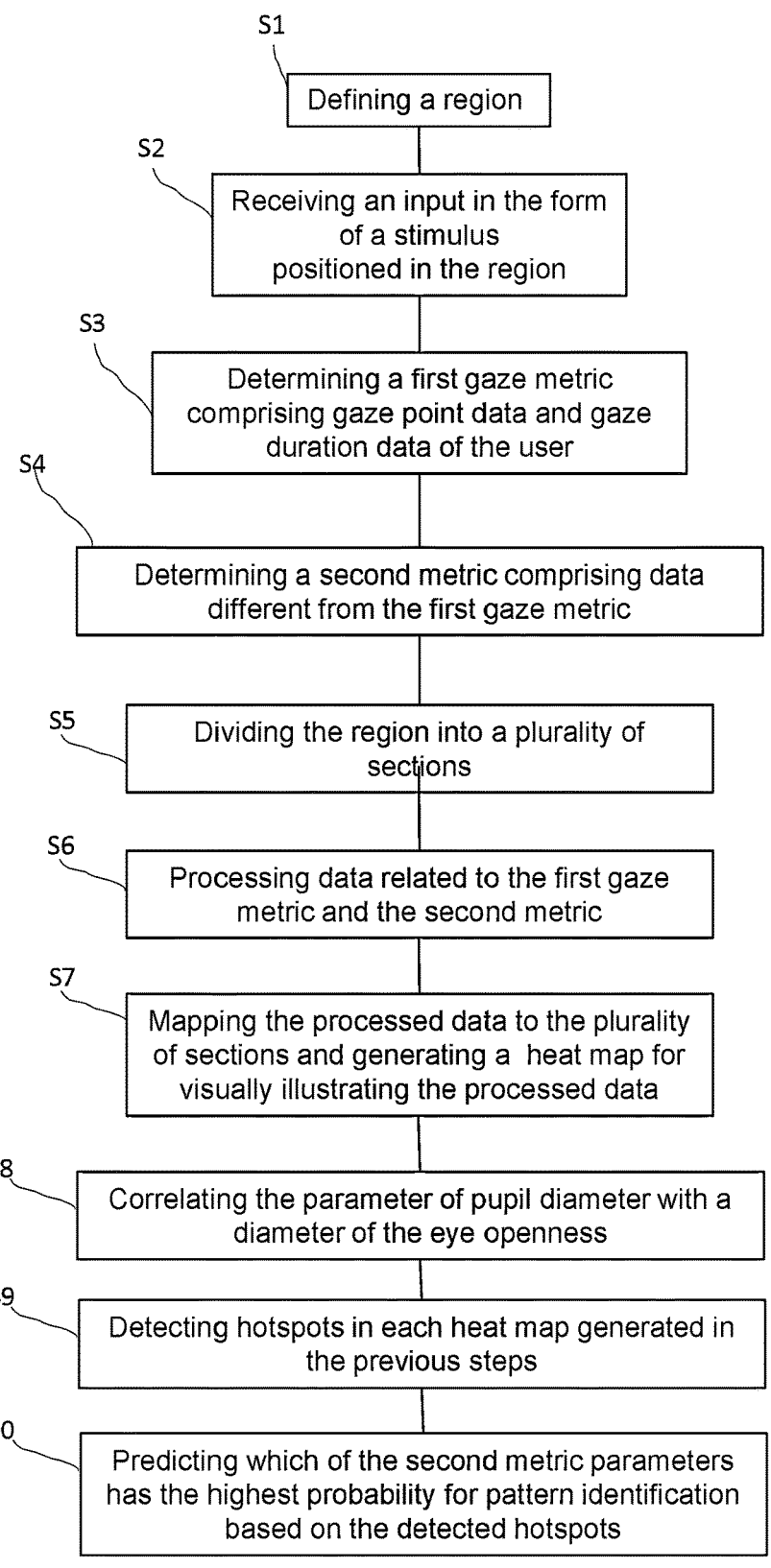

S1

Defining a region

S2

Receiving an input in the form
of a stimulus
positioned in the region

S3

Determining a first gaze metric
comprising gaze point data and gaze
duration data of the user

S4

Determining a second metric comprising data
different from the first gaze metric

S5

Dividing the region into a plurality of
sections

S6

Processing data related to the first gaze
metric and the second metric

S7

Mapping the processed data to the plurality
of sections and generating a heat map for
visually illustrating the processed data

S8

Correlating the parameter of pupil diameter with a
diameter of the eye openness

S9

Detecting hotspots in each heat map generated in
the previous steps

S10

Predicting which of the second metric parameters
has the highest probability for pattern identification
based on the detected hotspots

Fig. 9

METHOD TO DETERMINE UNIVERSAL HEAT MAP

CROSS-REFERENCE TO RELATED APPLICATION

The present application claims priority to Swedish patent application No. 2350413-7, filed 11 Apr. 2023, entitled "METHOD TO DETERMINE UNIVERSAL HEAT MAP," and is hereby incorporated by reference in its entirety.

TECHNICAL FIELD

The present invention relates to the field of eye tracking. In particular, the present disclosure relates to the generation of heat maps based on an observation of a user with an eye tracking system.

BACKGROUND OF THE INVENTION

Efforts have been made to provide heat maps which capture gaze duration and gaze points in relation to an image using an eye tracking system . Such heat maps are used in analysing user behaviour and basically show a representation of visual attention. Such heat maps are used in studies related to safety, marketing, research, product placement and similar purposes. Heat maps can be static or dynamic depending on the requirements. A static heatmap is showing a visualization of user attention independent of the time passed, thus as a summary. A dynamic heat map instead illustrates the behaviour over a period of time. By capturing the behaviour over a period of time, a dynamic heat map may provide more information as to how a user looks at an image. A dynamic heat map may also be called cumulative heat map since gaze duration or gaze points are captured over a period of time. For practical applications, dynamic heat maps are usually preferred. Both static and dynamic heat maps are covered by the disclosure herein.

In order to produce a heat map, typically gaze durations and gaze points, and/or the count thereof, are correlated in a map that is similar to a matrix representing a region that is being observed, the region comprising a stimulus. The gaze durations and gaze points are normalized, for example with gaussian kernels, prior to being entered into the map or matrix. For practical purposes, heat maps are often set up to overlay the captured data onto the image that has served as the stimulus. For example, in some versions the gaussian kernels may be cut off at the top in order to let a certain amount of image data pass through the gaze point data. Heat maps can be represented in several ways, for example by illustrating hot spots using a colour scale, in a luminance map where hot spots of the heat map are illustrated with higher illumination, or as focus maps whereby hotspots are displayed sharp while other parts of the heat map are visualized blurry or unsharp. Very often, the gaze data at a pixel level related to the image stimulus is captured via an eye tracking system. A pixel or square at the centre of the gaze, thus the pixel that the user currently fixates, is given a high value in a matrix while the surrounding pixels or squares are given lower values going to 0 (zero). Pixels or squares with the value 0 (zero) remain transparent, while the pixels or squares with a higher value in the matrix receive a more intense or brighter colour in the colour scale. Once the eye tracking system has collected data from a number of users or participants in study, a heat map is produced using this method based on the accumulated values. The resulting heat map presents pixels with no gaze data (zero value)

transparent, while the pixels having higher values have a brighter colour, for example from light green to red with yellow in between. The pixels with high attention have thus a warm colour while the pixels with low or no attention fade to transparency, thus showing the image. A heat map may also be established based on a single user or observer.

Depending on the objectives of such research, different metrics can be used.

Traditionally, the most common metric or type of data collected to form the basis for gaze-related heat maps, has been the duration of the gaze related to a point on the image or just simply the gaze point. Another common metric in gaze detection is fixation count. This metric ensures that every fixation or gaze point gets equal weight regardless of gaze duration. Both gaze duration and count data may be collected as absolute values or as a relative metric, where the input is scaled so that for example gaze fixation data from one user has the same weight as gaze fixation data from another user. Further, various filters and scales can be applied to adjust a heat map based on number of participants, sensitivity, gaze duration and so on.

For the purposes of studying user behaviour when confronted with visual stimulus, an image or a region or an observed region may be divided into areas of interest. A resulting heat map then represents the gaze data related to individual areas of interest, as collected using the eye tracking system. The disclosure herein is however not limited to areas of interest.

Traditional heat maps, however, have limitations as to their ability to illustrate data beyond gaze point and gaze duration. Current research and applications of heat maps have shown that there is an interest and demand to expand the data that heat maps are showing beyond the typical parameters of gaze point, and/or count thereof, and gaze duration, in particular in dynamic heat maps.

SUMMARY OF THE INVENTION

It is an objective of the present invention to provide a method for capturing eye tracking data that provides heat maps for various purposes depending on the parameters of interest.

It is also an objective to provide a system that is capable of performing the method, including a headset system that can apply and perform the method.

The inventors have discovered methods to extract further information from an observer or user using an eye tracking system, beyond gaze duration and/or gaze fixation. The inventors have realized that several other parameters relating to gaze can be extracted when an eye tracking system is observing a user, while still tracking gaze and gaze duration and then providing a heat map based on such further parameters. Examples of such parameters are mental workload, saccade velocity, saccade start and stop positions, regressions, and further examples are given herein. The inventors have further realized that analysing these parameters and disclosing them in heatmaps is of particular interest in behavioural research studies as the method allows to visualize patterns via heat maps depending on different chosen parameters.

Disclosed herein is a method for an eye tracking system comprising at least one camera, the method being configured to provide a heat map based on an observation of at least one user and comprising the steps of:
  receiving an input in the form of a stimulus;
  defining a region that is to be analysed, whereby the region comprises the stimulus;

determining a first gaze metric comprising gaze point data and gaze duration data of the user, the first gaze metric being determined in relation to the region comprising the stimulus and over a duration of time;

determining a second metric related to the user, the second metric comprising data different from the first gaze metric, the second metric being determined in relation to the region comprising the stimulus and over a duration of time;

dividing the region into a plurality of sections;

processing data related to the first gaze metric and the second metric, by allocating values to the sections, so that a heatmap can be generated based on these allocated values and the sections;

mapping the processed data to the plurality of sections for visualization in a heat map.

In the context of the present invention, whenever it is specified that a region to be analysed comprises a stimulus which has been received as an input, it is meant that such stimulus, once received as an input, is presented, or displayed, or shown, within the region to be analysed.

The described method allows to form heat maps for various parameters and provides a basis for decision making in various studies and research projects. It further provides important information for improving safety systems relating to visual or eye behaviour of users, operators or observers. In addition, it allows to identify not only where users spend most time in a region observing a stimulus but also how this time affects mental workload, for instance.

Based on the step of dividing the region, or the observed region, into a plurality of sections, each section can be used to present the gaze data according to the first gaze metric and the second metric and in the form of a heat map. The section may have a size that is adapted to the granularity that is required for the research that is performed.

In an embodiment the second metric is at least one parameter of: pupil diameter, eye openness, saccade start positions, saccade stop positions, saccade peak velocity positions, saccade peak velocities, a start position of a first saccade and/or a start position of a last saccade or a stop position of a first saccade and/or a stop position of a last saccade.

Any and all of the above parameters allow to produce heat maps that look substantially different from the traditional ones, as illustrated with a few examples in the figure description herein. Such different heat maps may help to make decisions for research for example related to human attention and/or behaviour in different situations.

In another embodiment, the method may further comprise the step of storing a separate heat map for each of the parameters of pupil diameter, eye openness, saccade start positions, saccade stop positions, saccade peak velocity positions, saccade peak velocities, a start position of a first saccade and/or a start position of a last saccade or a stop position of a first saccade and/or an stop position of a last saccade, on a computer readable storage medium for analysis purposes.

In yet another embodiment, the region, or the region being observed by the user, may be part of a display external to the eye tracking system and each section may correspond to at least a pixel of the display and wherein the first gaze metric and the second metric are determined in relation to each pixel of the display.

This may allow to produce heat maps related to screen attention of a user. In some embodiments this may include virtual reality (VR) or augmented reality (AR) applications.

In particular, AR may be one of a preferred field of application for the present invention.

Tracking gaze and parameter data related to each pixel may enhance the quality and detail of the produced heat map.

In an embodiment, the second metric may further comprise physiological data or behavioural data of the user. Such physiological or behavioural data may allow to produce other heat maps relating to such data.

In an embodiment, the region may be part of a display and the second metric may be any parameter of: cursor position and/or cursor click; and wherein the second metric is determined in relation to each pixel of the display.

In a further embodiment, the method may comprise the step of correlating the parameter of pupil diameter with a parameter related to a diameter of the eye openness, in order to determine mental workload of the user while looking at the region and the stimulus.

As mentioned, this may allow to detect mental workload of a user and therewith to build a heat map relating to such mental workload.

The method of the present invention may further comprise the steps of detecting hotspots in each heat map generated in the previous steps; and predicting which of the second metric parameters has the highest probability for pattern identification based on the detected hotspots.

The above may for example provide a basis for making a decision relating to a design of a research study.

In an embodiment, the above-described steps may be performed for at least a second region and/or at least a second stimulus.

Disclosed herein is also a system comprising a processor, a camera and a computer readable storage medium, the computer readable storage medium comprising instructions executable by the processor operative, or configured, to:

receive an input in the form of a stimulus;

define a region that is to be analysed, the region comprising the stimulus; determine a first gaze metric comprising gaze point data and gaze duration data of the user, the first gaze metric being determined in relation to the region comprising the stimulus and over a duration of time;

determine a second metric related to the user, said second metric comprising data different from the first gaze metric, the second metric being determined in relation to the region comprising the stimulus and over a duration of time;

divide the region into a plurality of sections;

process data related to the first gaze metric and the second metric by allocating values to the sections, so that a heatmap can be generated based on these allocated values and the sections;

map the processed data to the plurality of sections for visualization in a heat map.

In the system, the second metric may be any parameter of pupil diameter, eye openness, saccade start positions, saccade stop positions, saccade peak velocity positions and saccade peak velocities.

Saccade peak velocity positions and saccade peak velocities may be combined in a heat map or they may be visualized separately.

In another embodiment of the system, the processor may be further operative, or configured, to:

store each heat map relating to any of the parameters on the computer readable storage medium for analysis purposes.

The system and the processor of the system, respectively, may be designed to perform any of the above-described steps.

Disclosed herein is also a head mounted device comprising a system according to any of the above embodiments.

The system may further comprise a display.

A head mounted device may, in particular, be advantageous to detect user behaviour related to gaze and eyes' movement in particular and then illustrate the results in heat maps for pattern recognition.

Disclosed herein is also a computer program, comprising instructions which, when executed by a processor, cause the processor to:

receive an input in the form of a stimulus;

define a region that is to be analysed, whereby the region comprises the stimulus;

determine a first gaze metric comprising gaze point data and gaze duration data of the user, the first gaze metric being determined in relation to the region comprising the stimulus and over a duration of time;

determine a second metric related to the user, said second metric comprising data different from the first gaze metric, the second metric being determined in relation to the region comprising the stimulus and over a duration of time;

divide the region into a plurality of sections;

process data related to the first gaze metric and the second metric, by allocating values to the sections, so that a heatmap can be generated based on these allocated values and the sections;

map the processed data to the plurality of sections for visualization in a heat map.

Further, a computer readable storage medium may be provided whereby the computer readable storage medium may comprise a computer program according to the above.

The computer program may be configured to perform any of the steps disclosed herein.

Herein the following terms are used and herewith explained in more detail:

Region

A region herein may relate to a real-world view, a simulation, an image, an image on a display, a virtual image, a video or an augmented reality image. In general, the region is meant to be observed by a user.

Stimulus

A stimulus may be an object, a situation, a subject or any other substance or device or plant illustrated in the region. A stimulus may even be a moving object or moving subject or the like. It is to be noted that in the context herein and as an example either an entire text may be regarded as a stimulus or each word may be regarded or defined as a stimulus, this may change depending on the case or research at hand and the corresponding objectives.

Heat Map

A heat map describes a graphic representation that shows where a user attention e.g., in term of gaze and gaze duration, happened on a region or image. In order to produce a heat map, an image is typically divided into squares forming a grid or matrix. Within each square, the heat map shows the relative intensity of values captured by an eye tracking system by assigning each value a representation.

The representation may be shown in the form of darkness/brightness, cold colour/warm colour, blur/sharpness and so on. For example, those squares that are highest in their value-relative to the other squares-will be given a high brightness, a warm colour or a high sharpness, while those that are lower in their value will be given a cold colour, low brightness (darkness) or low sharpness. Other heat map illustrations may be used such as white/black shades. All these types of heat maps are herewith included in this disclosure, if not explicitly stated otherwise when the term heat map is used.

Hotspot

The term hotspot herein refers to heat maps and specifically refers to areas with high value presented in the form of hot colour, high brightness, or sharpness, to illustrate that these areas or sections are of particular relevance relating to the examined parameter. A hotspot may refer to a revisit, a regression, mental workload, saccade peak velocity and other parameters mentioned herein in relation to gaze point and gaze duration data. Hotspots may be used to decide if and how a certain gaze metric should be analysed.

Gaze

Gaze herein refers to the continuous viewing of an image, scenery or region. Gaze includes information as to where the subject, or user, is looking when presented with a (visual) stimulus. A heat map of gaze data therefore shows which parts were most frequently looked at and might even contain times or time periods of fixations by the gaze. Gaze relates to the eyes being fixed in steady intent look, often with specific attention. By observing the gaze of a subject, it is possible to determine in which direction a person looks and what the person looks at or which eye movement she/he follows.

Saccade

A saccade is a quick, simultaneous movement of both eyes between two or more phases of fixation in the same direction. When reading from one word to the next word, the reader typically performs a saccade, rather subconsciously, when the eyes jump from the previous word to the next word or just from focus point to focus point. In contrast, in smooth pursuit movements, the eyes move smoothly instead of in jumps. Saccades can be detected via eye tracking systems that track and observe the gaze of a person. Saccades serve as a mechanism for fixation and rapid eye movement. Analysing saccades can provide rather deep information of the visual behaviour of a person.

Areas of Interest

If specific details of a stimulus were to be examined, we would define Areas of Interest to analyse these specific details. If we wanted to know how much time each feature of an observed image was looked at, we should examine the fixations. It could for instance be decided to analyse specific sections of the observed region that are most important to look at and such region sections may be named areas of interest (AOI). As an example, the image may contain people, and one would want to quantify the number of times that an observer looks at the eyes of the people in the image. The coordinates for the eyes could be grouped to form an AOI and the results compared to those of similar clusters, or other AOIs, on the same image. Additionally, the behaviour of different observer-types, such as male or female, or different age groups etc. could also be also analysed in relation to specific AOIs.

Fixations

A fixation is regarded as a gaze that is maintained within the same region for more than a certain time period (in practice, this may be defined as within a specific degree radius of vision and lasting for over a certain number of milliseconds). A heat map built from fixation values therefore shows the number of times in which an individual pays focused attention to a particular part of an image. Heat maps may be created by default from gaze data such as fixations and gaze duration.

Fixation counts and fixation duration are the data points represented by traditional heat maps.

User Behaviour

The term user behaviour, or behaviour, describes how an observed person behaves consciously or sub-consciously in any way that can be visually determined. The main observation may be performed via the movement of eyes and the area surrounding the eyes. Other visual observations may however be included with the term user behaviour, such as emotional behaviour that can be visually detected. User behaviour may further include any other behaviour demonstrated when viewing an image, in addition to the behaviour captured using an eye tracking system. Such behaviour demonstrated may, for example, include mouse clicks and mouse cursor movement.

Further aspects and example embodiments are illustrated in the accompanying drawings and/or described in the following description.

BRIEF DESCRIPTION OF THE DRAWINGS

The present invention will now be described in more detail by way of embodiments and with reference to the enclosed drawings, in which:

FIG. 5a schematically illustrates a method to extract revisit and/or regression data using an eye tracking system;

FIG. 5b schematically illustrates the same text area as FIG. 4 but with a different heatmap obtained using the method according to the invention;

FIG. 8 schematically illustrates a method flow diagram according to a method of the invention;

FIG. 9 schematically illustrates a similar method as FIG. 8 but with additional steps, and FIG. 10 schematically illustrates a system according to the invention.

DETAILED DESCRIPTION

Throughout the following description, specific details are set forth in order to provide a more thorough understanding of the invention. However, the invention may be practiced without these particulars. In other instances, well known elements or steps have not been shown or described in detail to avoid unnecessarily obscuring the invention. Accordingly, the specification and drawings are to be regarded in an illustrative, rather than a restrictive sense.

Figure 1:
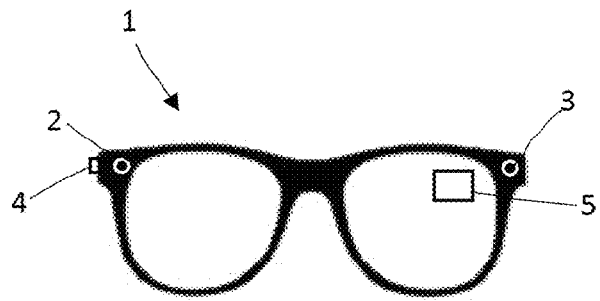
FIG. 1 schematically illustrates an eye tracking system.

FIG. 1 illustrates an eye tracking system 1 that may be used to perform any or all steps of a method as described herein to obtain a heat map. The eye tracking system 1 comprises at least one first camera 2 designed to capture image of the eyes of a wearer of the eye tracking system 1 and at least one communication and storing unit 4. The eye tracking system 1 may comprise a pair of first cameras 2, one for each eye. The communication and storing unit 4 may be used to communicate the image of the eyes of the user to a computer with higher computing capacity. The eye tracking system may additionally comprise a forward-looking camera 3 that is directed towards the field of vision of the wearer. Such a forward-looking camera 3 may provide information as to what image a user currently sees. The eye tracking system 1 may further comprise a display 5, which may even be a head up display 5, for presenting information to the wearer. The display 5 may alternatively be used for showing a region comprising a stimulus as explained referring to FIG. 2.

Figure 2:
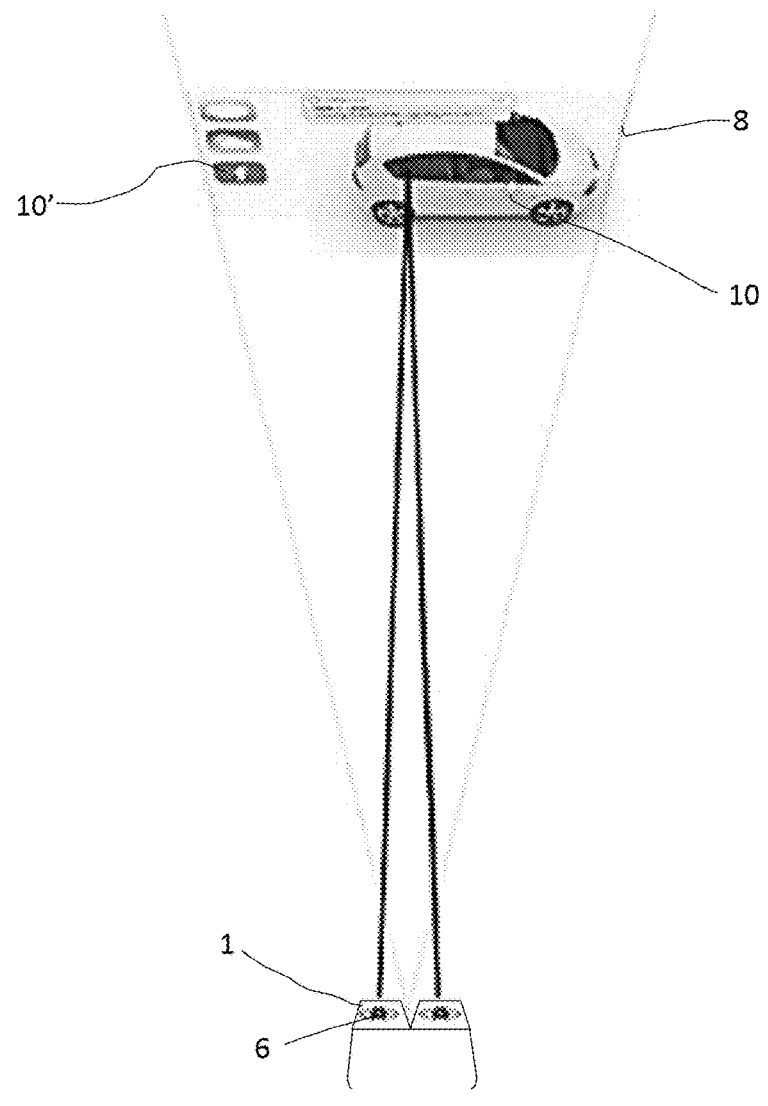
FIG. 2 schematically illustrates how an observer looks at a region containing at least one stimulus.

FIG. 2 illustrates a scene in which a user looks with her/his eyes 6 through an eye tracking system 1 towards a region 8, which comprises at least one stimulus 10, 10'. The region 8 that is being observed by a user, or observation region 8, comprises in the illustrated case a real object in the form of a car as stimulus 10 and an augmented reality stimulus 10' in the form of an icon that is projected onto the eye tracking system 1. The region 8 in the illustration of FIG. 2 may also be a display or screen, or part thereof. Using the eye tracking system 1 and the knowledge of what region 8 the user is looking at, a heat map can be established e.g., using gaze and gaze duration or fixation data.

Figure 3:
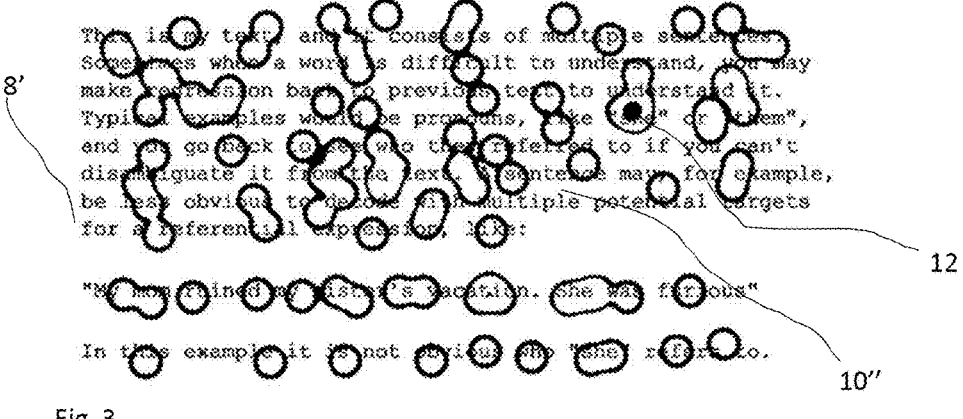
FIG. 3 schematically illustrates a heatmap of a text area.

Turning now to FIG. 3, a heat map of a region 8' is illustrated that comprises a text as stimulus 10". The heat map illustrated in FIG. 3 is obtained using an eye tracking system 1 which collects gaze and gaze duration data, employed to determine how a user is reading a text using her/his eyes. Such a heat map is illustrated using warm and cold colours, so that hotspots 12 can be easily detected. In the example illustrated in FIG. 3, a hotspot 12 is present at the pronoun "she" in the text: "My mom ruined my sister's vacation. She was furious". The user or reader may thus have stopped at the pronoun and looked at the word "she" for a longer time, because of its inherent ambiguity in the context of the sentence. Consequently, this specific section of the region has gotten a higher weight, or relevance, in the form of a warmer colour or darker dot located in the middle of the area covering the word "she".

Figure 4:
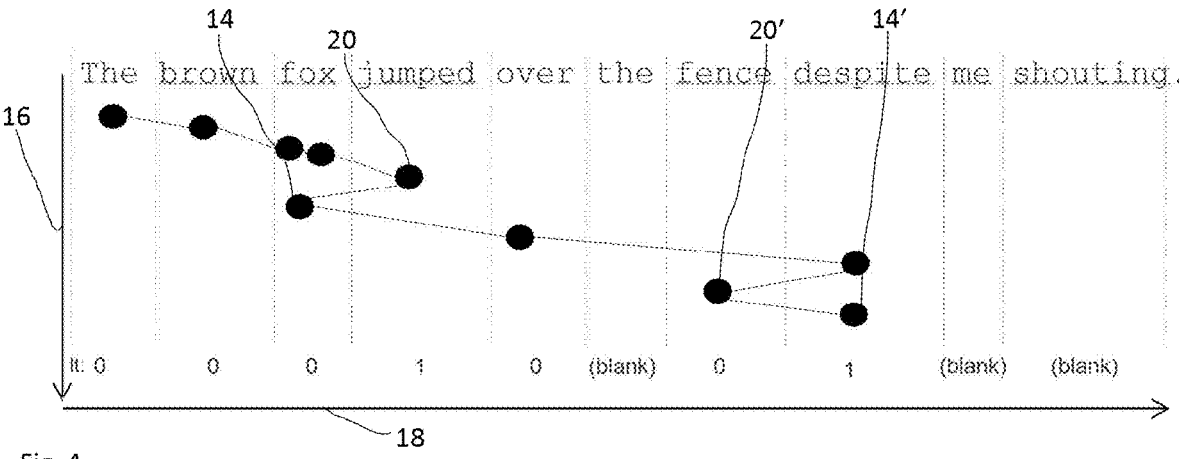
FIG. 4 schematically illustrates how a parameter of revisit and regression is obtained according to an aspect of the present invention.

FIG. 4 illustrates the analysis of a parameter related to gaze that goes beyond analysing gaze and gaze duration. The vertical axis 16 in FIG. 4 illustrates the time passed, while the horizontal axis 18 illustrates the progress of the user, in this case carrying out a task of reading a sentence, as captured by eye tracking. By tracking the eyes of a reader, one can establish if a certain section or position was revisited and also what caused the revisit. In the illustrated case, a revisit 14 was done on the word "fox", while the reason for revisit 14 and thus the regression 20 was caused by the word "jumped". A regression 20 is thus the reason for a saccade, or gaze jump, to a previous section, as detected by eye tracking. A saccade or gaze jump from one section to another sections provides two interesting parameters, revisit 14 and regression 20. Another example in FIG. 4 illustrates a regression 20' caused by the word "fence" and a revisit 14' to the word "despite". It is thus possible to generate heat maps based on either revisits 14, 14' or regressions 20, 20', delivering data that is different from straightforward gaze and/or gaze duration and/or count heat maps. In addition, it has to be noted that revisits 14, 14' or regressions 20, 20' even correlate with mental workload. In fact, a regression 20, 20' leads to a conclusion that the reader or observer has been thinking and checking on a specific fact, based on the stimulus 10, 10' that she/he is looking at.

FIG. 4 further illustrates how these events can be captured using a 0 (zero) and 1 (one) coding. Each regression 20 and regression 20' is represented as a 1 (one) to identify the actual event. This may also be performed by coding regression 20, and regression 20' differently, so that the two events can easily be distinguished.

As indicated in the previous paragraph and still referring to FIG. 4, it is possible to illustrate heat maps based on revisits 14, 14' or regressions 20, 20', no matter if the observer is looking at an image that shows a real-world situation, such as a text on paper or in a book, or a scenery or if the image is shown on a display or screen. How these revisits 14, 14' or regressions 20, 20' can be detected on a display will be explained in the following referring to FIGS. 5a and 5b.

FIG. 5a illustrates a graph that represents a region comprising a stimulus on it. In this example, the region is a display and the stimulus is a text or sentence. For illustrative purposes the stimulus in the form of the text is however not shown in FIG. 5. The first vertical axis 22 represents a y-coordinate position of a section or pixel on a screen, while the second vertical axis 24 represents an x-coordinate position of a section or pixel on a screen. The horizontal axis 26 represents elapsed time. The first set of bars 30 with inclined line pattern represents y-coordinates of gaze points while an observer is reading a sentence, while the second set of bars 28 with dotted pattern represents x-coordinates of gaze points while the observer is reading a sentence. When analysing FIG. 5a, one may realize that the observer is basically reading a sentence that is positioned on one line. Thus, the y-coordinate, which the first set of bars 30 represents, remains constant.

From FIG. 5a, one can determine if the gaze of the observer moved back to a previous recorded coordinate position. This is illustrated with the bar 28a that represents a specific word on the screen. The dashed line 32 illustrates that the x-coordinate, or x-coordinates for that matter, were visited again by the gaze, which results in the conclusion that a regression happened. Most likely the stimulus illustrated with bar 28b caused the regression. For practical purposes a revisit and a regression may be recorded if certain ranges of similar coordinates are revisited. This is indicated with bar 28a' in dashed lines. The exact coordinates, in the illustrated case x-coordinates, may thus stray a bit from the earlier visited x-coordinates, but such a threshold may be chosen by the operator or adjusted given the research or study at hand. Such a threshold may further depend on the stimulus that is shown. When using a text as stimulus, it might be rather easy to identify a revisit and therewith a regression, while another stimulus, such as a detailed picture or a moving image, may need lower thresholds to clearly identify revisits or regressions.

The above example is simplified in that it presumes that the y-coordinates stay the same during a regression. However, a regression may occur across both x- and y-coordinates, e.g., returning to a word located on a previous line of text.

FIG. 5b illustrates a heatmap based on the assumption that the text is now displayed on a screen and the detection of revisit explained with reference to FIG. 5a is herewith applied. The heat map illustrates that the observer made a revisit 14" to the word "she" of the sentence "My mom ruined my sister's vacation. She was furious". The revisit 14" is thus marked as hotspot. FIG. 5b thus only illustrates revisits 14" and for the sake of understanding and simplicity of example one can see that only the word "she" was revisited. It is to be noted that "she" in this case does not illustrate the regression. It was in fact chosen to only illustrate revisits 14" in the heat map of FIG. 5b. The regression might have its origin in another word in the example presented in FIG. 5b, most likely in the word "furious".

Figure 6A:
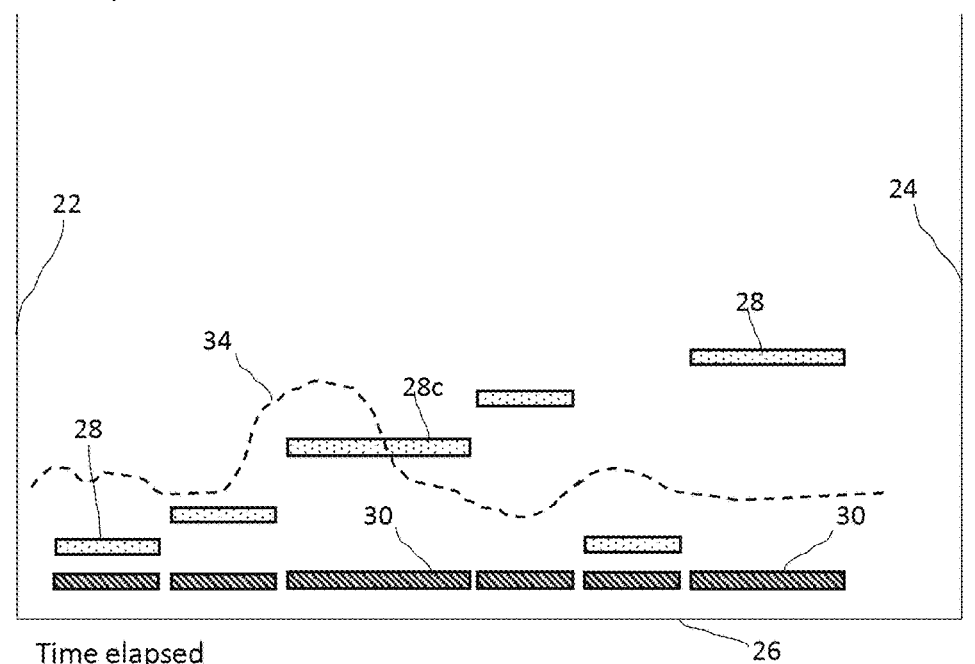
FIG. 6a schematically illustrates a similar view as FIG. 5a but in this case additionally illustrating mental workload of the reader.

FIG. 6a illustrates a similar view as FIG. 5a, with same reference numbers illustrating the same features as previously. In this example, however, the mental workload 34 is also indicated. In general, the mental workload of an observer can be detected by analysing pupil diameter and eye openness. The greater the pupil openness, the greater the mental workload 34. Thus, the mental workload 34 can be detected with an eye tracking system 1 (c.f. FIG. 1), particularly in relation to eye openness. Eye openness may be a metric to measure awareness (open eyes) or drowsiness (reduced eye openness). Using the same observation and example as previously, one can see that a mental workload peaks around the bar 28c, which represents a stimulus in the form of a word.

Figure 6B:
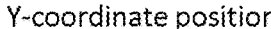
FIG. 6b schematically illustrates the same text area as FIGS. 4 and 5b but with another heat map obtained using the method according to the invention.

FIG. 6b illustrates another heat map that is originating from, or generated based on, the data disclosed in FIG. 6a and shows hotspots that relate to mental workload. The mental workload 34 is illustrated as a hotspot 34' in FIG. 6b. The hotspot 34' is correlated to the gaze, since mental workload detections make sense when coupled to the gaze of the observer and correlatable to an actual position on the region observed, as for the text shown on a screen in the example of FIG. 6b.

Figure 7A:
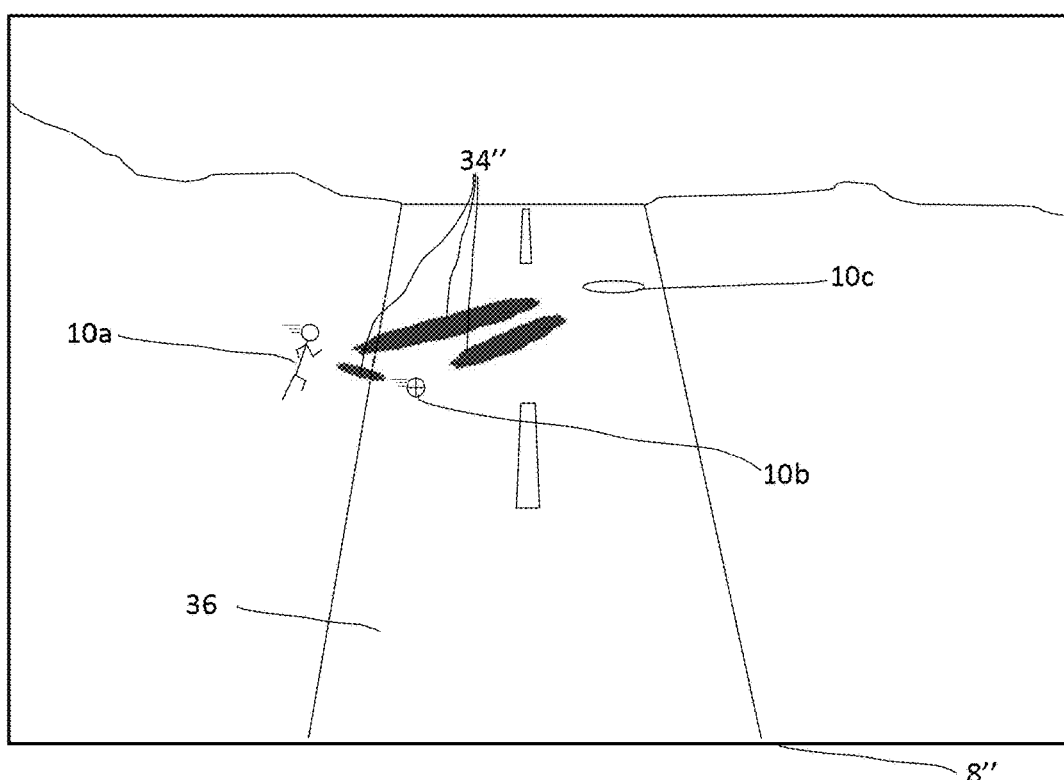
FIG. 7a schematically illustrates a heat map obtained using the method according to the invention, the heat map relating to a real-world image or a simulation thereof.
Figure 7B:
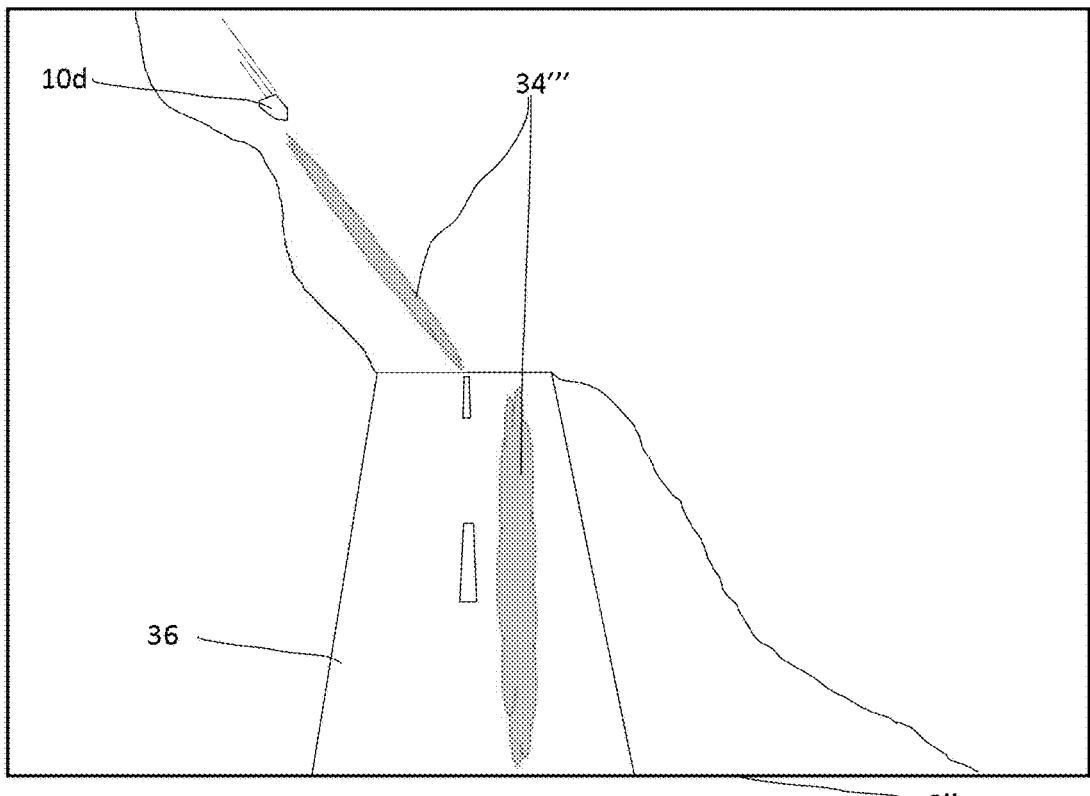
FIG. 7b schematically illustrates another heat map obtained using the method according to the invention, the heat map illustrating another real-world image or simulation thereof.

FIGS. 7a and 7b illustrate another heat map based on another metric-in this case peak velocity of a saccade. FIGS. 7a and 7b illustrate the vision of a driver through a car windscreen, which is represented by region 8". An eye tracking system (not shown in FIGS. 7a and 7b) is observing the driver and then producing heatmaps as illustrated in FIGS. 7a and 7b based on saccade peak velocities and gaze. FIGS. 7a and 7b represent region 8" at different points of time.

In FIG. 7a, the region 8" comprises a scenery where a driver is driving a vehicle along a road 36 as seen, for example through a windscreen of a vehicle. The region 8" may be a real-life image or a simulation. The region 8" comprises three stimuli 10a, 10b and 10c, a first stimulus 10a being a young person chasing a second stimulus 10b in the form of a ball that is rolling towards the road 36. Further, on the road is a third stimulus 10c in the form of a pothole.

One can imagine that this situation puts pressure on the driver and his gaze starts automatically jumping between the first, second and third stimuli 10a, 10b, 10c.

The metric that is detected is the peak velocity of the saccade when moving the gaze between the first, second and third stimulus 10a, 10b, 10c. Based on that, the region 8" can be illustrated as a heat map that shows hotspots 34" that relate to peak velocity of saccades in the region 8". A purpose to detect peak velocities of saccades becomes clear when FIG. 7a is compared to FIG. 7b. For the sake of illustration, one may assume that a few hours have passed between the two situations. Further, it is to be noted that the heat map is a virtual image, or at least a virtual image, but, for the sake of understanding, the heat map and the windscreen, and thus the region 8", are overlaid with one another in both FIGS. 7a and 7b.

FIG. 7b illustrates a similar view as FIG. 7a, with the region 8" also being a windscreen of a vehicle. The region 8" comprises the road 36 or another road and a stimulus 10d in the form of a falling rock that threatens to fall on the road on which the driver is driving the vehicle. One can imagine that the driver is assessing the risk of the rock/stimulus 10d falling onto the road and thus estimating a braking distance needed. This will lead to exemplary hotspots 34'" for peak velocity of saccades. This time, however, the hotspots 34'" are shown in a lighter colour, or just brighter, to illustrate that the peak velocity of saccades in the heat map of FIG. 7b is lower.

The lowering of the peak velocity of saccades in turn provides the information that the driver is becoming increasingly tired, since peak velocity of saccades correlates directly to tiredness. By comparing or observing peak velocities of saccades, it may be determined whether a person is tired or not, as the peak velocities of a tired person are slower than that of an alert person.

The peak velocity of saccade hotpots may also be called glances that illustrate how the eyes of driver behave depending on the presented stimulus.

FIGS. 7a and 7b may show a real-life situation where an eye tracking system is installed in a vehicle and tracks saccade peak velocities to detect if the driver is tired or not; or it may relate to a simulation for research purposes, also using an eye tracking system.

FIG. 8 illustrates a method according to the present invention. The method is for an eye tracking system comprising at least one camera and it is configured to provide a heat map based on an observation of at least one user comprising the steps of:

defining S1 a region 8, 8', 8", 8'" observed by a user that is to be analysed;
  receiving S2 an input in the form of a stimulus 10, 10a-10d whereby the stimulus 10, 10a-10d is positioned, or received, within the region 8, 8', 8", 8'";
  determining S3 a first gaze metric comprising gaze point data and gaze duration data of the user, the first gaze metric being determined in relation to the region 8, 8', 8", 8'" comprising the stimulus 10, 10a-10d and over a duration of time;
  determining S4 a second metric related to the user, the second metric comprising data different from the first gaze metric, the second metric being determined in relation to the region 8, 8', 8", 8'" comprising the stimulus 10, 10a-10d and over a duration of time;
  dividing S5 the region 8, 8', 8", 8'" into a plurality of sections;
  processing S6 data related to the first gaze metric and the second metric by allocating values to the sections;

mapping S7 the processed data to the plurality of sections and generating a heat map for visually illustrating the processed data, based on the allocated values and the sections.

The above method allows to generate heat maps for various parameters and metrics related to gaze and gaze duration and further different parameters that can be detected with an eye tracking system, according to, but not exhaustively, the previous embodiments illustrated referring to FIGS. 1 to 7b. In particular, the second metric may be a different one from those mentioned above, i.e., illustrated peak saccade velocity 34", mental workload 34, or revisits 14, 14' and regressions 20, 20'.

In general, the second metric may comprise any of pupil diameter, mouse positions, mouse clicks, eye openness, duration/count from only whole or partial fixations, saccade start positions, saccade stop positions, saccade peak velocity positions and/or saccade peak velocities.

Additionally, the second metric may comprise parameters that are of higher order or even require additional equipment to detect but still related to the first gaze metric as mentioned above. Such parameters may be mental workload related to human factors and applied sciences, start of regression movement related to reading research, end of regression movement related to reading research and/or start position of glance event related to driving research.

Still other parameters of the second metric may relate to conditional parameters such as start position of first/last saccade, end position of first/last saccade, end position of saccades leading out of area of interest, start position of saccade leading into area of interest and/or pupil diameter of gaze points from an eye with eye openness with a threshold for example greater than 4 mm.

Further the sections may be coordinates, or squares, or clusters of pixels, or even single pixels.

The method may further comprise the step of storing S11 a separate heat map for each of the parameters of pupil diameter, eye openness, saccade start positions, saccade stop positions, saccade peak velocity positions, saccade peak velocities, a start position of a first saccade and/or a start position of a last saccade or a stop position of a first saccade and/or an stop position of a last saccade, on a computer readable storage medium for analysis purposes.

FIG. 9 illustrates another method according to the invention, whereby the steps S1 to S7 are the same as the ones illustrated relating to FIG. 8.

According to FIG. 9, the method may additionally comprise the step of correlating S8 the parameter of pupil diameter with a diameter of the eye openness, in order to determine mental workload of the user while looking at the region and the stimulus.

In addition, the method further comprises the optional steps of detecting S9 hotspots in each heat map generated in the previous steps and predicting S10, which of the second metric parameters has the highest probability for pattern identification based on the detected hotspots.

One can understand that the method allows to produce different heat maps that illustrate various parameters according to the above and may provide a basis for making research decisions and, in particular, provide a basis for developing a framework for a research project.

Figure 10:
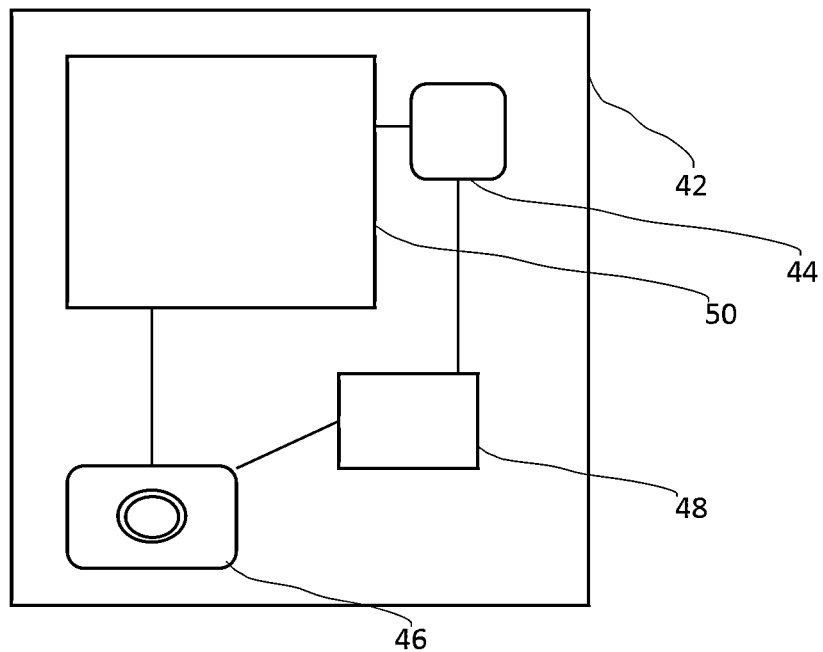

FIG. 10 illustrates a system 42 comprising a processor 44, a camera 46 and a computer readable storage medium 48, the computer readable storage medium 48 comprising instructions executable by the processor 44 to perform any of the illustrated method steps according to FIG. 8 or 9. The system may optionally also comprise a display 50. The processor 44, the camera 46, the computer readable storage medium 48 and the display 50 may be electronically connected to one another so that data can be transferred between each of them.

Various features are described herein as being present in "some embodiments" in "another embodiment" or "still another embodiment" and so on including embodiments referring explained referring to the figures. Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" "another embodiment" or "still another embodiment" and so on possess feature A and "some embodiments" possess feature B should be interpreted as an express indication that the inventors also contemplate embodiments which combine features A and B (unless the description states otherwise or features A and B are fundamentally incompatible).

The invention claimed is:

1. A method for an eye tracking system comprising at least one camera, the method being configured to provide a heatmap based on an observation of at least one user and comprising the steps of:

defining a region that is to be analysed;

receiving an input in the form of a stimulus whereby the stimulus is positioned within the region;

determining a first gaze metric comprising gaze point data and gaze duration data of the user, the first gaze metric being determined in relation to the region comprising the stimulus and over a duration of time;

determining a second metric related to the user, the second metric comprising data different from the first gaze metric, the second metric being determined in relation to the region comprising the stimulus and over a duration of time, wherein the second metric is at least one parameter of pupil diameter, eye openness, saccade start positions, saccade stop positions, saccade peak velocity positions, saccade peak velocities, a start position of a first saccade and/or a start position of a last saccade or a stop position of a first saccade and/or a stop position of a last saccade;

dividing the region into a plurality of sections;

processing data related to the first gaze metric and the second metric by allocating values to the sections, so that a heatmap can be generated based on these allocated values and the sections; mapping the processed data to the plurality of sections and generating a heatmap for visually illustrating the processed data; and storing a separate heatmap for each of the parameters of the second metric on a computer readable storage medium for analysis purposes.

2. The method according to claim 1, wherein the region is part of a display external to the eye tracking system and each section corresponds to a pixel of the display and wherein the first gaze metric and the second metric are determined in relation to each pixel of the display.

3. The method according to claim 1, wherein the second metric further comprises physiological data or behavioural data.

4. The method according to claim 3, wherein the region is part of a display and wherein the second metric is any parameter of: cursor position and/or cursor click; and

wherein the cursor position and/or cursor click is determined in relation to the region of the display.

5. The method according to claim 1, comprising the step of:

correlating the parameter of pupil diameter with a diameter of the eye openness, in order to determine mental workload of the user while looking at the region and the stimulus.

6. The method according to claim 1, comprising the steps of:

detecting hotspots in each heatmap generated in the previous steps; and predicting which second metric has the highest probability for pattern identification based on the detected hotspots.

7. The method according to claim 1, comprising the step of performing any of the above steps for at least a second region and/or at least a second stimulus.

8. A system comprising a processor, a camera and a computer readable storage medium, the computer readable storage medium comprising instructions executable by the processor operative to:

define a region that is to be analysed;

receive an input in the form of a stimulus whereby the stimulus is positioned within the region;

determine a first gaze metric comprising gaze point data and gaze duration data of the user, the first gaze metric being determined in relation to the region comprising the stimulus and over a duration of time;

determine a second metric related to the user, said second metric comprising data different from the first gaze metric, the second metric being determined in relation to the region comprising the stimulus and over a duration of time, wherein the second metric is at least one parameter of pupil diameter, eye openness, saccade start positions, saccade stop positions, saccade peak velocity positions, saccade peak velocities, a start position of a first saccade and/or a start position of a last saccade or a stop position of a first saccade and/or a stop position of a last saccade;

divide the region into a plurality of sections;

process data related to the first gaze metric and the second metric by allocating values to the sections, so that a heatmap can be generated based on these allocated values and the sections; map the processed data to the plurality of sections for visualization in a heatmap; and store a separate heatmap for each of the parameters of the second metric on a computer readable storage medium for analysis purposes.

9. The system according to claim 8, wherein the defined region that is to be analysed is part of a display external to the eye tracking system and each section corresponds to a pixel of the display and wherein the first gaze metric and the second metric are determined in relation to each pixel of the display.

10. A head mounted device comprising a system according to claim 8.

11. The head mounted device according to claim 10, further comprising a display.

12. A non-transitory computer readable storage medium comprising a computer program, comprising instructions which, when executed by a processor, cause the processor to:

define a region that is to be analysed;

receive an input in the form of a stimulus whereby the stimulus is positioned within the region;

determine a first gaze metric comprising gaze point data and gaze duration data of the user, the first gaze metric being determined in relation to the region comprising the stimulus and over a duration of time;

determine a second metric related to the user, said second metric comprising data different from the first gaze metric, the second metric being determined in relation to the region comprising the stimulus and over a duration of time, wherein the second metric is at least one parameter of pupil diameter, eye openness, saccade start positions, saccade stop positions, saccade peak velocity positions, saccade peak velocities, a start position of a first saccade and/or a start position of a last saccade or a stop position of a first saccade and/or a stop position of a last saccade;

divide the region into a plurality of sections;

process data related to the first gaze metric and the second metric by allocating values to the sections, so that a heatmap can be generated based on these allocated values and the sections;

map the processed data to the plurality of sections for visualization in a heatmap; and store a separate heatmap for each of the parameters of the second metric on a computer readable storage medium for analysis purposes.

\* \* \* \* \*